United States Patent
Phillips et al.

(10) Patent No.: US 11,608,818 B2
(45) Date of Patent: Mar. 21, 2023

(54) AEROSOL-GENERATING SYSTEM WITH PUMP

(71) Applicant: Altria Client Services LLC, Richmond, VA (US)

(72) Inventors: Shaun Phillips, Peterborough (GB); Bruce Renfrew, Hilltop (GB); Ben Mazur, Bristol (GB); Ben Bright, Gloucestershire (GB); Rui Nuno Batista, Morges (CH)

(73) Assignee: Altria Client Services LLC, Richmond, VA (US)

( * ) Notice: Subject to any disclaimer, the term of this patent is extended or adjusted under 35 U.S.C. 154(b) by 352 days.

(21) Appl. No.: 16/527,501

(22) Filed: Jul. 31, 2019

(65) Prior Publication Data

US 2019/0350266 A1    Nov. 21, 2019

Related U.S. Application Data

(63) Continuation of application No. 15/388,742, filed on Dec. 22, 2016, now Pat. No. 10,398,174, which is a
(Continued)

(30) Foreign Application Priority Data

Dec. 22, 2015    (EP) .................................... 15202158

(51) Int. Cl.
*H05B 1/02*    (2006.01)
*F04B 19/00*   (2006.01)
(Continued)

(52) U.S. Cl.
CPC .............. *F04B 13/02* (2013.01); *A24F 40/42* (2020.01); *A24F 40/48* (2020.01); *A24F 40/485* (2020.01);
(Continued)

(58) Field of Classification Search
None
See application file for complete search history.

(56) References Cited

U.S. PATENT DOCUMENTS 6,234,167 B1 *   5/2001   Cox .................. A61M 15/0083
                                                       128/200.14
2002/0078946 A1   6/2002   Sprinkel et al.
(Continued)

FOREIGN PATENT DOCUMENTS

CN    1205849 A    1/1999
CN    1222089 A    7/1999
(Continued)

OTHER PUBLICATIONS

Office Action dated Jan. 20, 2021 in Chinese Application No. 201680069574.1.
(Continued)

*Primary Examiner* — Thor S Campbell
(74) *Attorney, Agent, or Firm* — Harness, Dickey & Pierce, P.L.C.

(57) ABSTRACT

An aerosol-generating system may include a liquid storage portion configured to hold liquid aerosol-forming substrate, a vaporizer including a heating element with an internal passage at least partially defined by a surface of the heating element, and a micro pump configured to deliver liquid aerosol-forming substrate from the liquid storage portion to the internal passage of the heating element, such that the vaporizer is configured to heat the delivered liquid aerosol-forming substrate at the internal passage to a temperature sufficient to volatilize at least a part of the delivered liquid aerosol-forming substrate. The micro pump may be configured to deliver a particular amount of liquid aerosol-forming substrate to the internal passage based on the micro pump performing an individual pump cycle.

19 Claims, 4 Drawing Sheets

Related U.S. Application Data continuation of application No. PCT/EP2016/080245, filed on Dec. 8, 2016.

(51) Int. Cl.
| | |
|---|---|
| *A24F 40/42* | (2020.01) |
| *A24F 40/48* | (2020.01) |
| *A24F 40/485* | (2020.01) |
| *A24F 40/50* | (2020.01) |
| *A24F 15/015* | (2020.01) |
| *F04B 13/02* | (2006.01) |
| *F04B 43/04* | (2006.01) |
| *F04B 23/02* | (2006.01) |
| *F04B 53/10* | (2006.01) |
| *F04B 17/03* | (2006.01) |
| *A24F 40/10* | (2020.01) |

(52) U.S. Cl.
CPC .............. *A24F 40/50* (2020.01); *F04B 17/03* (2013.01); *F04B 19/006* (2013.01); *F04B 23/02* (2013.01); *F04B 43/046* (2013.01); *F04B 53/10* (2013.01); *H05B 1/0244* (2013.01); *A24F 15/015* (2020.01); *A24F 40/10* (2020.01); *H05B 2203/021* (2013.01); *H05B 2203/022* (2013.01)

(56) References Cited

U.S. PATENT DOCUMENTS

| | | | |
|---|---|---|---|
| 2003/0132219 A1* | 7/2003 | Cox | A61M 11/041 219/486 |
| 2003/0136404 A1 | 7/2003 | Hindle et al. | |
| 2004/0081624 A1* | 4/2004 | Nguyen | A61K 9/0078 424/44 |
| 2008/0085103 A1* | 4/2008 | Beland | A61L 9/035 392/390 |
| 2012/0090630 A1* | 4/2012 | Hon | A24F 47/002 131/273 |
| 2012/0230659 A1* | 9/2012 | Goodman | F22B 1/282 392/395 |
| 2014/0060554 A1 | 3/2014 | Collett et al. | |
| 2014/0064715 A1 | 3/2014 | Greim et al. | |
| 2014/0283855 A1 | 9/2014 | Hawes et al. | |
| 2014/0353856 A1 | 12/2014 | Dubief | |
| 2015/0027456 A1* | 1/2015 | Janardhan | A24F 47/008 131/328 |
| 2015/0047662 A1* | 2/2015 | Hopps | A24F 47/008 131/329 |
| 2015/0114409 A1 | 4/2015 | Brammer et al. | |
| 2015/0117842 A1 | 4/2015 | Brammer et al. | |
| 2015/0216237 A1* | 8/2015 | Wensley | A24F 47/008 131/273 |
| 2017/0020192 A1* | 1/2017 | Fregonese | H05B 3/0014 |

FOREIGN PATENT DOCUMENTS

| | | |
|---|---|---|
| CN | 1289271 A | 3/2001 |
| CN | 101522244 A | 9/2009 |
| CN | 104114048 A | 10/2014 |
| EP | 0957959 A2 | 11/1999 |
| EP | 2047880 A1 | 4/2009 |
| EP | 2519122 B1 | 4/2014 |
| JP | S62-262981 A | 11/1987 |
| WO | WO-2008/015918 A1 | 2/2008 |
| WO | WO-2011/122474 A1 | 10/2011 |
| WO | WO-2013/027249 A1 | 2/2013 |
| WO | WO-2014/150552 A1 | 9/2014 |
| WO | WO-2014/153515 A1 | 9/2014 |
| WO | WO-2014/177687 A1 | 11/2014 |

OTHER PUBLICATIONS

Notice of Allowance dated Feb. 19, 2021 issued in corresponding European Patent Application No. 16806177.8.
Chinese Office Action dated Apr. 28, 2020 for corresponding Chinese Application No. 201680069574.1.
Chinese Office Action dated Jul. 21, 2020 for corresponding Chinese Application No. 201680072365.2.
Chinese Office Action dated Sep. 2, 2020 for corresponding Chinese Application No. 201680069574.1.
Russian Office Action dated Jan. 31, 2020 for corresponding Russian Application No. 2018126759/12(042501).
European Office Action dated Mar. 12, 2020 for corresponding European Application No. 16806177.8.
Chinese Office Action dated May 11, 2021 for corresponding Chinese Application No. 201680069574.1, and English-language translation thereof.
European Communication dated Oct. 23, 2020 for corresponding European Application No. 16806177.8.
Japanese Office Action dated Nov. 30, 2020 for corresponding Japanese Application No. 2018-530602, and English-language translation thereof.
Extended European Search Report for European Application No. 15202158.0 dated Jun. 6, 2015.
International Search Report and Written Opinion dated Feb. 14, 2017 issued in corresponding International Application No. PCT/EP2016/080245.
International Preliminaty Report on Patentability dated Jun. 26, 2018 issued in corresponding International Application No. PCT/EP2016/080245.
Office Action dated Jul. 5, 2021 issued in corresponding Japanese Patent Application No. 2018-530602.
Russian Office Action dated Apr. 30, 2020 for corresponding Russian Application No. 2018126759.
Japanese Decision to Grant for corresponding Application No. 2018-530602, dated Mar. 7, 2022, English translation included herewith.
Mexican Office Action dated May 12, 2022, for corresponding Mexican Application No. MX/a/2018/007403.

* cited by examiner

AEROSOL-GENERATING SYSTEM WITH PUMP

CROSS-REFERENCE TO RELATED APPLICATIONS

This application is a continuation of U.S. application Ser. No. 15/388,742, filed on Dec. 22, 2016, which is a continuation of, and claims priority to, international application no. PCT/EP2016/080245, filed on Dec. 8, 2016, and further claims priority under 35 U.S.C. § 119 to European Patent Application No. 15202158.0, filed Dec. 22, 2015, the entire contents of each of which are incorporated herein by reference.

BACKGROUND

Field

One or more example embodiments relate to aerosol-generating systems, including electrically operated dispersion generating systems, also referred to interchangeably as electronic vaping devices, that are configured to generate an aerosol, including a vapor, based on vaporizing an aerosol-forming substrate that is liquid and.

Description of Related Art

Some types of aerosol-generating systems include electronically-operated vaping devices. Handheld electrically operated vaping devices are known that consist of a device portion comprising a battery and control electronics, a cartridge comprising a supply of aerosol-forming substrate held in a liquid storage portion, and an electrically operated vaporizer. A cartridge may include both a supply of aerosol-forming substrate held in the liquid storage portion and a vaporizer is sometimes referred to as a "cartomizer". The vaporizer typically comprises a coil of heater wire wound around an elongate wick soaked in the liquid aerosol-forming substrate held in the liquid storage portion. The cartridge may include, in addition to the liquid storage portion and the vaporizer, an outlet-end insert through which air may be drawn to draw an aerosol generated by the vaporizer through the outlet-end insert and out of the aerosol-generating system.

EP 0 957 959 B1 discloses an electrically operated aerosol generator for receiving liquid material from a source, the aerosol generator comprising a pump for pumping the liquid material in metered amounts from the source through a tube with an open end, and a heater surrounding the tube. When heating the liquid material by the heater, the volatized material expands by exiting the open end of the tube.

In some cases, residues are created based on heating a liquid aerosol-forming substrate to generate an aerosol. In capillary tubes, the residues can cause clogging. This effect can alter liquid transport properties. Furthermore, the liquid material is heated indirectly: First the tube or a capillary wick is heated which in turn heats the liquid material. Heat can therefore be lost during the energy transfer process.

It would be desirable to provide an improved aerosol-generating system with a low-maintenance liquid transport system and reduced power consumption.

SUMMARY

According to some example embodiments, an aerosol-generating system may include: a liquid storage portion configured to hold a liquid aerosol-forming substrate; a vaporizer including a heating element having a structure defining an open-ended internal passage; and a micro pump configured to deliver liquid aerosol-forming substrate from the liquid storage portion to the internal passage of the heating element. The vaporizer may be configured to heat the delivered liquid aerosol-forming substrate at the internal passage to a temperature sufficient to volatilize at least a part of the delivered liquid aerosol-forming substrate.

The micro pump may be configured to deliver a determined amount of liquid aerosol-forming substrate from the liquid storage portion to the internal passage of the heating element based on the micro pump performing an individual pump cycle.

The aerosol-generating system may include a chamber configured to receive liquid aerosol-forming substrate delivered from the liquid storage portion by the micro pump. The micro pump may include an outlet and the micro pump is configured to deliver the liquid aerosol-forming substrate through the outlet of the micro pump. The heating element may be located inside the chamber and proximate to the outlet of the micro pump.

The aerosol-generating system may include a tubing segment configured to deliver the liquid aerosol-forming substrate from the micro pump to the vaporizer.

The vaporizer may be arranged downstream of an open end of the tubing segment.

The tubing segment may include a capillary tube.

The vaporizer may include a heating coil extending around a portion of the tubing segment.

The vaporizer may include a heating coil extending from the tubing segment in a longitudinal direction.

The vaporizer may include a conical heater extending from the tubing segment in a longitudinal direction.

The liquid storage portion may include a rigid container and a one-way valve that is configured to direct air into the rigid container upon delivering liquid aerosol-forming substrate from the liquid storage portion to the internal passage of the heating element.

The liquid storage portion may include a flexible container including at least one movable wall, the at least one movable wall configured to reduce a volume of the liquid storage portion to cause liquid aerosol-forming substrate to be delivered from the liquid storage portion to the internal passage of the heating element.

The liquid storage portion may include a septum configured to enable refilling of the liquid storage portion with liquid aerosol-forming substrate.

The liquid storage portion may include a one-way valve between the liquid storage portion and the micro pump.

The flow rate of the delivered liquid aerosol-forming substrate through the micro pump may be within 0.5 to 2 microliters per second.

The aerosol-generating system may include a main unit and a cartridge, the cartridge configured to be removably coupled to the main unit, the main unit including a power supply, the liquid storage portion being within the cartridge, the micro pump being located in the main unit.

The cartridge may include the liquid storage portion.

According to some example embodiments, a method may include: controlling a micro pump to deliver liquid aerosol-forming substrate from a liquid storage portion to an internal passage within a heating element of a vaporizer; and controlling the vaporizer to heat the delivered liquid aerosol-forming substrate at the internal passage to a temperature sufficient to volatilize at least a part of the delivered liquid aerosol-forming substrate.

The controlling the micro pump may include causing the micro pump to deliver a determined amount of liquid aerosol-forming substrate from the liquid storage portion to the internal passage of the heating element based on causing the micro pump performing an individual pump cycle.

The controlling the micro pump may include causing the micro pump to deliver liquid aerosol-forming substrate at a flow rate that is within 0.5 to 2 microliters per second.

The micro pump may include an outlet, the heating element may be located inside a chamber and proximate to the outlet of the micro pump, and the controlling the micro pump may include causing the micro pump to deliver the liquid aerosol-forming substrate through the outlet of the micro pump.

The vaporizer may include a conical heater extending from a tubing segment along a longitudinal axis of at least the tubing segment, an inner surface of the conical heater at least partially defining the internal passage as a conical passage extending along the longitudinal axis.

BRIEF DESCRIPTION OF THE DRAWINGS

Embodiments of the invention will now be described, by way of example only, with reference to the accompanying drawings, in which.

DETAILED DESCRIPTION

Figure 1A:
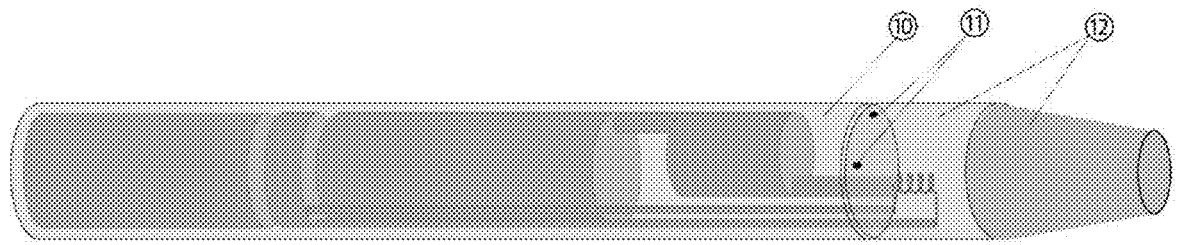
FIG. 1A is a perspective and a topside view of an aerosol-generating system according to some example embodiments.
Figure 1A:
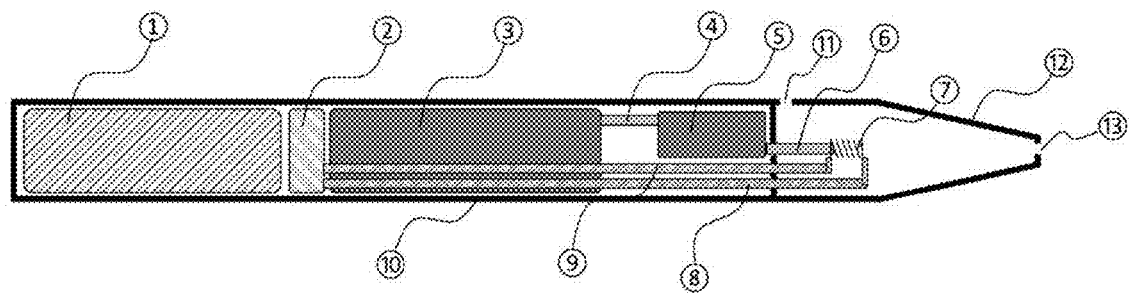

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, and/or elements, but do not preclude the presence or addition of one or more other features, integers, steps, operations, elements, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, regions, layers and/or sections, these elements, regions, layers and/or sections should not be limited by these terms. These terms are only used to distinguish one element, region, layer or section from another region, layer or section. Thus, a first element, region, layer or section discussed below could be termed a second element, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Some example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to some example embodiments an aerosol-generating system may include a liquid storage portion configured to store liquid aerosol-forming substrate, a vaporizer comprising a heating element having a structure defining an open-ended internal passage, and a micro pump configured to deliver liquid aerosol-forming substrate from the liquid storage portion to the internal passage of the heating element (e.g., to one or more surfaces, structures, etc. at least partially defining the internal passage), wherein the vaporizer is configured to heat the delivered liquid aerosol-forming substrate at the internal passage to a temperature sufficient to volatilize at least a part of the delivered liquid aerosol-forming substrate. The structure of the heating element may include one or more surfaces, including one or more internal surfaces ("inner surfaces") that at least partially define the internal passage. The defined internal passage may extend at least partially through an interior of the heating element and may extend along a longitudinal axis. The longitudinal axis may be a longitudinal axis of the vaporizer, the heating element, one or more various elements of the aerosol-generating system, some combination thereof, or the like.

The aerosol-generating system may be configured to pump a determined amount of liquid aerosol-forming substrate from the liquid storage portion to the internal passage of the heating element. Based on being deposited to the heating element directly, the liquid aerosol-forming substrate may remain in a liquid state until it reaches the heating element. Consequently, the production of residues can be reduced and/or minimized during liquid transport. Such an aerosol-generating system configured to enable such a reduction of residue production may thus include one or more cartridges in which vaporizers are absent. Due to the improved liquid transport, tubing segments and vaporizers may not need to be disposed once the liquid storage portion is empty. By including a pump instead of a capillary wick or any other passive medium to draw liquid, the aerosol-generating system may be configured to transport a particular ("determined") amount of liquid aerosol-forming substrate to the heating element. In some example embodiments, the aerosol-generating system may be configured to pump liquid aerosol-forming substrate based on a command signal (e.g., "on-demand"), for example in response to a drawing of air at least partially through the aerosol-generating system.

The micro pump may be configured to enable on-demand delivery of liquid aerosol-forming substrate at a low flow rate of, for example, approximately 0.5 to 2 microliters per second for intervals of variable or constant duration. The micro pump may be configured to be carefully tuned in order to deliver a particular ("determined," "appropriate," etc.) amount of liquid aerosol-forming substrate to the heating element. Consequently, the aerosol-generating system may be configured to determine the amount of deposited liquid aerosol-forming substrate based on the amount ("quantity") of pump cycles.

The micro pump may be configured to pump liquid aerosol-forming substrates that are characterized by a relatively high viscosity as compared to water. The viscosity of a liquid aerosol-forming substrate may be in a range from about 10 to 500 Millipascal-seconds. In some example embodiments, the viscosity of liquid aerosol-forming substrate may be in a range from about 17 to 86 Millipascal-seconds.

The micro pump may be a single micro pump, for example a micro pump comprising a pump inlet, a pump outlet, and a pump chamber between the pump inlet and the pump outlet. Liquid aerosol-forming substrate to be pumped is available at the pump inlet. The single micro pump may be based on a piezoelectric diaphragm in combination with a passive check valve at each of the pump inlet and the pump outlet. A piezo ceramic mounted on a membrane may be configured to be deformed upon applying a voltage. The resulting down stroke causes liquid aerosol-forming substrate to be displaced out of the pump chamber. The check valve may be configured to reduce and/or prevent liquid aerosol-forming substrate backflow between usages, for example backflow into the cartridge. The pump may control the flow direction of the liquid through the pump from the inlet to the outlet. When the voltage applied to the piezo ceramic decreases, the corresponding piezo deformation may cause an upstroke of the membrane. Liquid aerosol-forming substrate may be drawn from the pump inlet and may fill the pump chamber. The single micro pump may perform up to several hundreds of such pump cycles per second, for example up 100 pump cycles per second, 200 pump cycles per second, 300 pump cycles per second, 400 pump cycles per second, and/or 500 pump cycles per second.

The micro pump may comprise a plurality of single micro pumps in series where the pump outlet of a single micro pump is connected to the pump inlet of the following single micro pump. In some example embodiments, the micro pump comprises two single micro pumps coupled in series. To ensure a proper flow of liquid through the series of single micro pumps, the piezo transducers may, for example, be configured to be operated sequentially after each other. In some example embodiments where the micro pump includes two single micro pumps, the piezo transducer corresponding to the first single micro pump may be configured to be actuated to perform an up and down stroke, and then the piezo transducer corresponding to the second single micro pump may be configured to be actuated to perform an up and down stroke. One pump cycle (e.g., an individual pump cycle) of a micro pump with a plurality of single micro pumps may include sequential actuation of the piezo transducers of one single micro pump after the other.

Adjusting the flow rate may include increasing the energy utilized to vaporize a greater amount of delivered liquid aerosol-forming substrate at the heating element. Therefore, the aerosol-generating system may be configured to adjust temperature settings of the vaporizer in accordance to the liquid flow rate.

The aerosol-generating system may include electric circuitry configured to control a temperature of the heating element. In some example embodiments, the electric circuitry is configured to control the temperature of the heating element based on at least one of a preheat duration parameter, a hold high duration parameter, a hold low duration parameter, and a hold timeout duration parameter, as explained in detail below.

The electric circuitry may be configured to cause the aerosol-generating system to operate in a preheat mode when the aerosol-generating has been powered on. The electric circuitry may be configured to cause the heating element to be heated, to generate heat, etc. constantly until the heating element reaches a particular (or, alternatively, predetermined) operating temperature. The operating temperature may be 250° C. The duration of the preheat mode may be controlled based on the preheat duration parameter. In some example embodiments, the preheat duration parameter is set to a value between 3000 and 4000 milliseconds. Under normal conditions, the aerosol-generating system may reach its operating temperature within the preheat duration. Once the operating temperature is reached, the electric circuitry may be configured to cause the micro pump to be activated for at least one pump cycle to transport an amount of liquid aerosol-forming substrate through the micro pump to configure the aerosol-generating system to generate an aerosol based on vaporization of the liquid aerosol-forming substrate.

The aerosol-generating system may be configured to then operate in a temperature hold mode until the electric circuitry detects a drawing of air at least partially through the aerosol-generating system, or until a hold timeout duration is reached as defined by the value of the hold timeout duration parameter.

The electric circuitry may be configured to, when causing the aerosol-generating system to operate in the temperature hold mode, cause a sequence of heating pulses to be sent to the heating element which can have the effect of maintaining a lower preheat temperature at the heating element that is below the operating temperature until the hold timeout is reached. The lower preheat temperature may be 150° C.

A heating pulse may comprise a sequence of a high and a low electrical signal, for example wherein the sending of the high signal causes electrical power to be supplied to the heating element for the value of the hold high duration parameter, and wherein the sending of the low signal causes the supply of electrical power to the heating element to be ceased for the duration of the value of the hold low duration parameter. The duration of the temperature hold mode may be controlled by the electric circuitry based on a value of the hold timeout duration parameter, before the aerosol-generating system enters a cool-down mode.

The practical effect of these different modes can be that the aerosol-generating system is configured to provide reduced latency with regard to generating an aerosol based on determining that an aerosol is commanded to be generated (e.g., based on detecting that at least a threshold flow rate of air is being drawn through at least a portion of the aerosol-generating system, based on detecting receipt of a command from an interface of the aerosol-generating system, some combination thereof, etc.), as the heating element is already hot during regular vapings, but the aerosol-generating system may be configured to conserve electrical power expenditure when turned on but not causing aerosol to be generated. The electric circuitry may be configured to, based on detecting an input received from a sensor, replace an alternating signal of the sequence of heating pulses with a constant signal to cause the temperature of the heating element to be brought back to the operating temperature.

Once a drawing of air through at least a portion of the aerosol-generating system has been detected and the heating element has reached the operating temperature, the electric circuitry may activate the micro pump and set a determined flow rate to deliver liquid aerosol-forming substrate to the internal passage of the heating element for the duration of the drawing of air at least partially through the aerosol-generating system.

Based on determining that the drawing has stopped, the aerosol-generating system may return to the temperature hold mode. If no input is detected during the temperature hold duration, the system may automatically cool down and wait for input.

Both the micro pump and the heating element may be triggered by a detection system. In some example embodiments, the micro pump and the heating element may be triggered by pressing an on-off button, held for the duration of a drawing of air at least partially through the aerosol-generating system.

In some example embodiments, the micro pump is configured to deliver a determined amount of liquid aerosol-forming substrate from the liquid storage portion to the internal passage of the heating element based on performing one pump cycle.

In some example embodiments, the aerosol-generating system further comprises a chamber into which the liquid aerosol-forming substrate is delivered, and wherein the heating element is located inside the chamber downstream of and/or proximate to an outlet of the micro pump through which the liquid aerosol-forming substrate is delivered.

As used herein, the terms 'upstream', 'downstream', 'proximal', 'distal', 'front' and 'rear', are used to describe the relative positions of elements, or portions of elements, of the aerosol-generating system in relation to the direction in which air may be drawn through at least a portion of the aerosol-generating system by an adult vaper during vaping.

The aerosol-generating system may comprise an outlet end through which an aerosol may be drawn during vaping. The outlet end may also be referred to as the proximal end. Air may be drawn out of the aerosol-generating system through the proximal or outlet end of the aerosol-generating system. The aerosol-generating system comprises a distal end opposed to the proximal or outlet end. The proximal or outlet end of the aerosol-generating system may also be referred to as the downstream end and the distal end of the aerosol-generating system may also be referred to as the upstream end. Elements, or portions of elements, of the aerosol-generating system may be described as being upstream or downstream of one another based on their relative positions between the proximal, downstream or outlet end and the distal or upstream end of the aerosol-generating system.

In some example embodiments, the aerosol-generating system further comprises a tubing segment through which the liquid aerosol-forming substrate may be delivered from the micro pump to the vaporizer. The tubing segment may be configured to deliver the liquid aerosol-forming substrate directly to the heating element. The tubing segment may be arranged to deliver the liquid aerosol-forming substrate towards an open end of the internal passage in the heating element. The tubing segment may extend from the liquid storage portion in a direction towards an open end of the internal passage in the heating element. The vaporizer may be arranged ("located") downstream of and/or proximate to an open end of the tubing segment. The vaporiser may extend around a portion of the tubing segment.

The tubing segment, also referred to as tube, may be a nozzle. The tubing segment may comprise any appropriate material, for example glass, silicon, metal, for example stainless steel, or plastics material, for example PEEK. The size of the tube may match that of the pump outlet. For example, the tube may have a diameter of about 1 to 2 millimeters but other sizes are possible. The tubing segment may be a 2 milliliters capillary nozzle (for example glass from Drummond) connected to the micro pump via a silicon tubing. In some example embodiments, the tubing segment comprises a capillary tube. The cross-section of the capillary tube may be circular, ellipsoid, triangular, rectangular or any other suitable shape to convey liquid. At least a width dimension of the cross-sectional area of the capillary tube may be sufficiently small such that on the one hand capillary forces are present. At the same time, the cross-sectional area of the capillary tube may be sufficiently large such that a suitable amount of liquid aerosol-forming substrate can be conveyed to the heating element. In general, the cross-sectional area of the capillary tube is in some examples below 4 square millimeters, below 1 square millimeter, or below 0.5 square millimeters.

The vaporizer may comprise a heating coil extending from the tubing segment in longitudinal direction. The heating element, which may be a coil, may extend around a portion of the tubing segment. The heating coil may be mounted transverse to the tubing segment. The heating coil may overlap with the open end of the tubing segment for up to 3 millimeters, for up to 1 millimeter. In some example embodiments, there may be a distance between the open end of the tubing segment and the heating coil. The length of the heating coil may be 2 millimeters to 9 millimeters, and/or 3 millimeters to 6 millimeters. The diameter of the heating coil may be chosen such that one end of the heating coil can be mounted around the tubing segment. The diameter of the heating coil may be 1 millimeter to 5 millimeters, and/or 2 millimeters to 4 millimeters.

The vaporizer may comprise a conical heater extending from the tubing segment in longitudinal direction. The conical heater may overlap with the open end of the tubing segment. In some examples, there may be a distance of 0.1 millimeters to 2 millimeters between the open end of the tubing segment and the conical heater, and/or 0.1 millimeters to 1 millimeter. The slant height of the conical heater may be 2 millimeters to 7 millimeters, and/or 2.5 millimeters to 5 millimeters. The diameter of the conical heater in cross-sectional view may increase, when following the slant height from one end to the other, from a first diameter to a second diameter. The first diameter may be 0.1 millimeters to 2 millimeters, and/or 0.1 millimeters to 1 millimeter. The second diameter may be 1.2 millimeters to 3 millimeters, and/or 1.5 millimeters to 2 millimeters. In some example embodiments, the conical heater is arranged such that the liquid aerosol-forming substrate exiting from the tubing segment passes the conical heater at the first diameter before the second diameter. The first diameter of the conical heater may be such that one end of the conical heater may be mounted around the tubing segment.

The vaporizer may a solid or mesh surface. The vaporizer may comprise a mesh heater. The vaporizer may comprise an arrangement of filaments.

The vaporizer may comprise at least one of a solid, flexible, porous, and perforated substrate onto which the heating element may be, for example, at least one of mounted, printed, deposited, etched, and laminated. The substrate may be a polymeric or ceramic substrate.

In some example embodiments, the liquid storage portion comprises a rigid container and a one-way valve that may be configured to let ("direct") air into the container upon delivering liquid aerosol-forming substrate from the liquid storage portion to the internal passage of the heating element.

In some example embodiments, the liquid storage portion comprises a flexible container including at least one movable wall that may be configured to reduce the volume of the liquid storage portion based on delivering liquid aerosol-forming substrate from the liquid storage portion to the deposition region of the heating element.

In some example embodiments, the liquid storage portion comprises a septum for refilling the liquid storage portion with liquid aerosol-forming substrate.

In some example embodiments, the liquid storage portion comprises a one-way valve arranged between the liquid storage portion and the micro pump. The one-way valve may control the liquid flow from the liquid storage portion to the inlet of the micro pump and may be configured to avoid or reduce reflux back to the liquid storage portion once the micro pump stops pumping.

In some example embodiments, the pump is configured to induce a flow rate of the delivered liquid aerosol-forming substrate through the micro pump that is within 0.5 to 2 microliters per second.

In some example embodiments, the aerosol-generating system comprises a main unit and a cartridge, wherein the cartridge may be removably coupled to the main unit, wherein the main unit may comprise a power supply, wherein the liquid storage portion may be included in the cartridge, and wherein the micro pump may be included in the main unit. In some example embodiments, the main unit further comprises the vaporizer. The main unit may comprise the tubing segment.

The aerosol-generating system according to some example embodiments may further comprise electric circuitry connected to the vaporizer and to an electrical power source. The electric circuitry may be configured to monitor (e.g., "determine") the electrical resistance of the vaporizer, and may be configured to control the supply of power from the power supply to the vaporizer based on the determined electrical resistance of the vaporizer.

The electric circuitry may comprise a controller with a microprocessor, which may be a programmable microprocessor. The electric circuitry may comprise further electronic elements. The electric circuitry may be configured to regulate a supply of power to the vaporizer. Power may be supplied to the vaporizer continuously following activation of the system or may be supplied intermittently, such as on a vaping-by-vaping basis. The power may be supplied to the vaporizer in the form of pulses of electrical current.

The aerosol-generating system may include a power supply (e.g., a battery), for example within the main body of the housing. The power supply may be a form of charge storage device such as a capacitor. The power supply may be rechargeable and may have a capacity that enables the storage of enough energy for one or more vapings (e.g. generating of vapor). For example, the power supply may have sufficient capacity to allow for the continuous generation of aerosol for a period of around six minutes or for a period that is a multiple of six minutes. In another example, the power supply may have sufficient capacity to allow for a predetermined number of vapings or discrete activations of the heater assembly.

For allowing ambient air to enter the aerosol-generating system, a wall of the housing of the aerosol-generating system, including a wall opposite the vaporizer, e.g., a bottom wall, is provided with at least one semi-open inlet. The semi-open inlet may be configured to direct air to enter the aerosol-generating system, but no air or liquid to leave the aerosol-generating system through the semi-open inlet. A semi-open inlet may for example be a semi-permeable membrane, permeable in one direction only for air, but is air- and liquid-tight in the opposite direction. A semi-open inlet may for example also be a one-way valve. In some example embodiments, the semi-open inlet is configured to direct air to pass through the inlet only if specific conditions are met, for example a particular and/or minimum depression in the aerosol-generating system and/or a particular volume of air passing through the valve or membrane.

The liquid aerosol-forming substrate may be a substrate configured to release volatile compounds that can form an aerosol. The volatile compounds may be released based on heating the liquid aerosol-forming substrate. The liquid aerosol-forming substrate may comprise plant-based material. The liquid aerosol-forming substrate may comprise tobacco. The liquid aerosol-forming substrate may comprise a tobacco-containing material containing volatile tobacco flavor compounds, which are released from the liquid aerosol-forming substrate upon heating. The liquid aerosol-forming substrate may alternatively comprise a non-tobacco-containing material. The liquid aerosol-forming substrate may comprise homogenized plant-based material. The liquid aerosol-forming substrate may comprise homogenized tobacco material. The liquid aerosol-forming substrate may comprise at least one aerosol-former. The liquid aerosol-forming substrate may comprise other additives and ingredients, such as flavorants.

The aerosol-generating system may be an electrically operated vaping system. In some example embodiments, the aerosol-generating system is portable. The aerosol-generating system may have a total length between approximately 30 millimeters and approximately 150 millimeters. The aerosol-generating system may have an external diameter between approximately 5 millimeters and approximately 30 millimeters.

According to some example embodiments, a cartridge for the aerosol-generating system may include the liquid storage portion. The liquid storage portion may comprise an outlet that is configured to connect to the inlet of the micro pump.

In some example embodiments, the cartridge comprises a cover that covers the outlet of the liquid storage portion. The cover may be a pulled sticker or a seal, for example a film seal, which may be configured to protect the cartridge before the outlet of the cartridge is connected to the inlet of the micro pump. The cover could be removed from the cartridge before the cartridge is inserted into the main unit. In some example embodiments, the cover is configured to be punctured or pierced so that the cover opens automatically upon inserting the cartridge into the main unit.

The cartridge may be a disposable article configured to be replaced with a new cartridge once the liquid storage portion of the cartridge is empty or below a minimum volume threshold. In some example embodiments, the cartridge is pre-loaded with liquid aerosol-forming substrate. The cartridge may be refillable.

The cartridge and its elements may be made of thermoplastic polymers, such as polyether ether ketone (PEEK).

According to some example embodiments, there is provided a method for generating aerosol, comprising:
(i) storing liquid aerosol-forming substrate in a liquid storage portion,
(ii) delivering, by a micro pump, liquid aerosol-forming substrate from the liquid storage portion to an internal passage within a heating element of a vaporizer, and
(iii) heating, by the vaporizer, the delivered liquid aerosol-forming substrate at the internal passage to a temperature sufficient to volatilize at least a part of the delivered liquid aerosol-forming substrate.

Features described in relation to one aspect may equally be applied to other aspects of the inventive concepts.

Figure 1B:
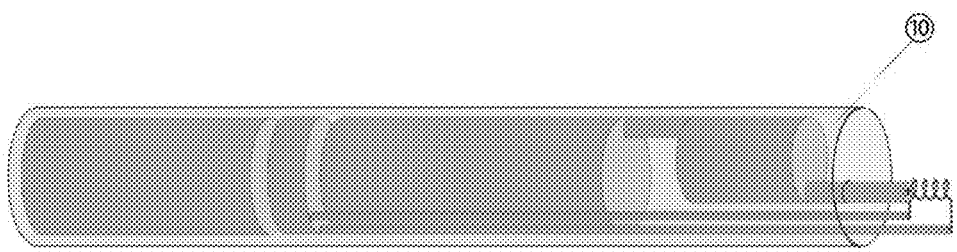
FIG. 1B is a perspective view of an aerosol-generating system according to some example embodiments.
Figure 1B:
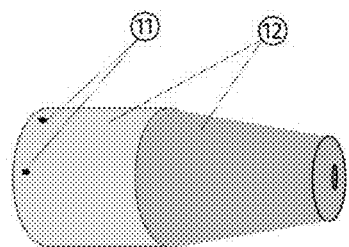

FIGS. 1A and 1B are schematic illustrations of an aerosol-generating system. The aerosol-generating system comprises a main unit and a refillable or exchangeable cartridge including a liquid storage portion 3. The main unit comprises a main body 10 and an outlet-end insert 12. The main body 10 contains a power supply 1, for example a battery such as a lithium iron phosphate battery, electronic circuitry 2, a cavity configured to hold a cartridge, a micro pump 5 with an inlet and an outlet, and a vaporizer 7. Electrical connectors 8, 9 are provided at the sides of the main body 10 to provide an electrical connection between the electric circuitry 2, the power supply 1, and the vaporizer 7. The vaporiser 7 may be a heating coil defining an internal passage. Tubing segment 4 may connect an outlet of the liquid storage portion to the inlet of the micro pump. Tubing segment 6 leads the flow of liquid aerosol-forming substrate from the outlet of the micro pump 5 to the internal passage of the heating element of the vaporizer 7. The tubing segment 6 may be straight and may transport the liquid aerosol-forming substrate directly to the heating element. The outlet-end insert 12 comprises a plurality of air inlets 11 and an outlet 13. Air may be drawn through the outlet 13 to draw air from the air inlets 11, through the outlet-end insert 12 to the outlet 13. The outlet-end insert 12 may include one or more internal baffles that are configured to force the air flowing through the outlet-end insert 12. The vaporizer 7 may be configured to heat the liquid aerosol-forming substrate directly after the liquid aerosol-forming substrate exits the tubing segment 6.

The cartridge including the liquid storage portion 3 may be configured to be inserted into a cavity within the main body 10. The cartridge should be replaceable, e.g., if and/or when the aerosol-forming substrate provided in the cartridge is depleted. The main housing 10 may include a slider that is configured to be moved to expose the cavity of the main housing 10 if and/or when a new cartridge is inserted into the cavity. The slider may be configured to be moved by the new cartridge. The new cartridge may be inserted into the exposed cavity. The outlet of the liquid storage portion is configured to connect to the inlet of the micro pump 5. The main unit may be portable.

Figure 2:
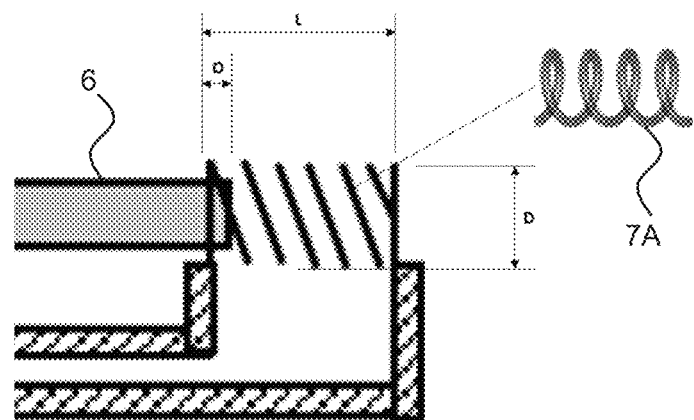
FIG. 2 is a topside view of a tubing segment and a heating coil for an aerosol-generating system according to some example embodiments.

FIG. 2 shows a detail of the open ended side of the tubing segment 6. A heating coil 7A is mounted onto the open ended side of the tubing segment 6 such that the heating coil 7A extends from the tubing segment 6 in longitudinal direction. Liquid aerosol-forming substrate may exit at the open end of the tubing segment 6. The liquid aerosol-forming substrate may exit the tubing segment 6 into the internal passage of the coil 7A. The heating coil 7A is in and around the flow of liquid so that the liquid aerosol-forming substrate is directly heated. The heating coil 7A has a length L, a diameter D, and an overlap O with the tubing segment 6.

Figure 3A:
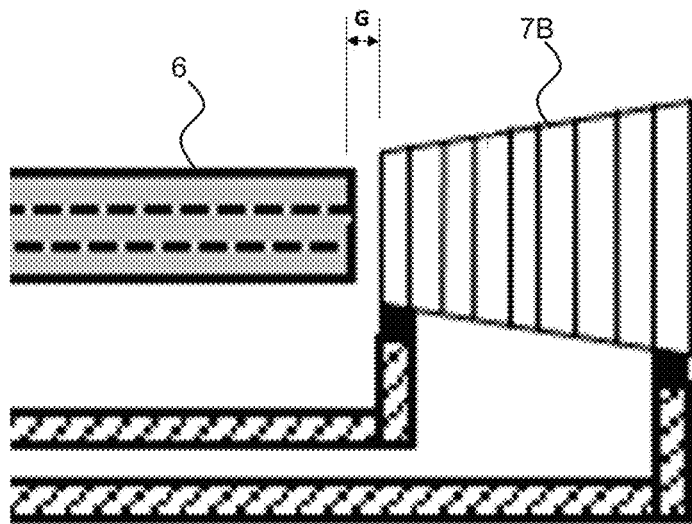
FIG. 3A is a topside view of a tubing segment and a conical heater for an aerosol-generating system according to some example embodiments.
Figure 3B:
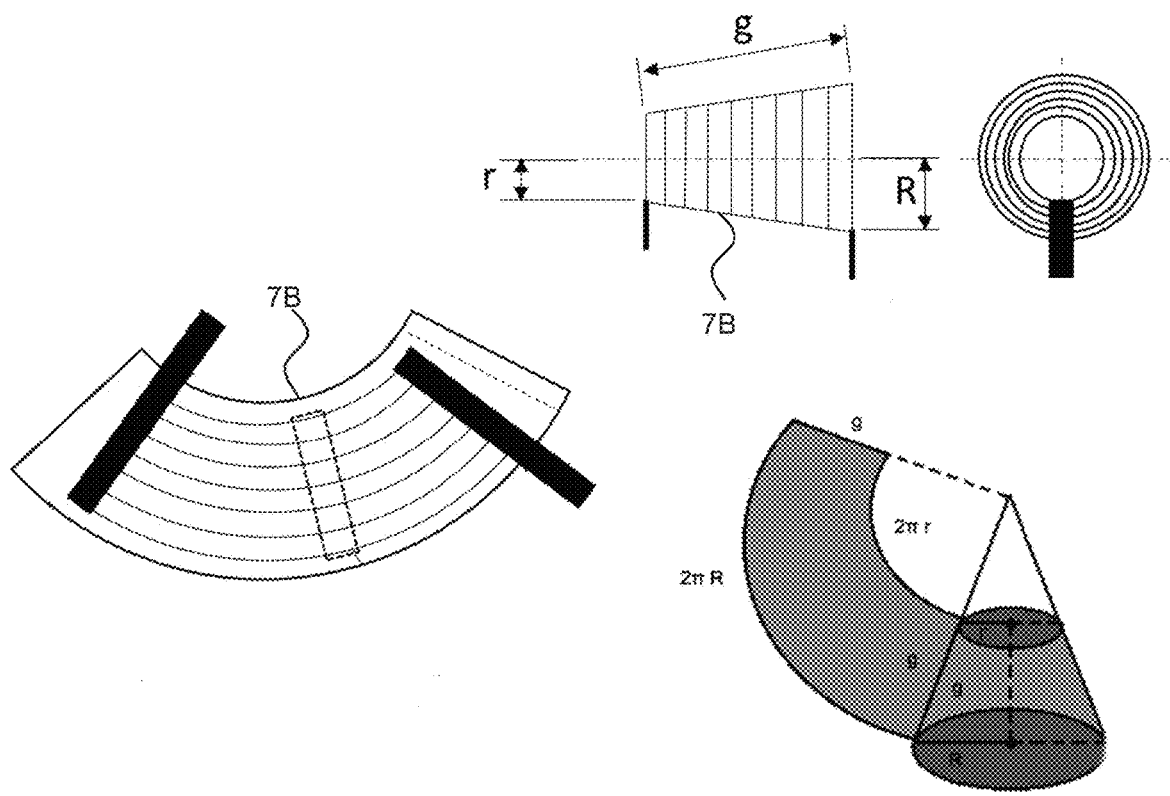
FIG. 3B is schematic illustration for making the conical heater shown in FIG. 3A.

FIG. 3A shows a detail of the open ended side of the tubing segment 6. A conical heater 7B is mounted downstream of and/or proximate to the open ended side of the tubing segment 6 such that the conical heater 7B extends from the tubing segment 6 in longitudinal direction. Liquid aerosol-forming substrate exits at the open end of the tubing segment 6 into an internal passage at least partially defined by one or more surfaces, including one or more inner surfaces, of the conical heater 7B. As shown in FIG. 3B, the internal passage may extend through at least a portion of an interior of the conical heater 7B, such that the boundaries of the internal passage are at least partially defined by the structure (e.g., one or more surfaces) of the conical heater 7B. As further shown in FIG. 3B, the internal passage may extend along a longitudinal axis of the conical heater 7B. The conical heater 7B is in and around the flow of liquid so that the liquid aerosol-forming substrate is directly heated. There is a distance G between the cone end side of the conical heater 7B and the tubing segment 6.

FIG. 3B is a schematic illustration of making the conical heater 7B from a flat substrate. The conical heater 7B has a slant height g with a radius that increases from a first radius r to a second radius R. As shown in FIG. 3B, the conical heater 7B may include one or more inner surfaces that at least partially define an internal passage extending through an interior of the conical heater 7B along a longitudinal axis of the conical heater 7B. As shown in FIG. 3B, the internal passage may be open-ended.

Figure 4:
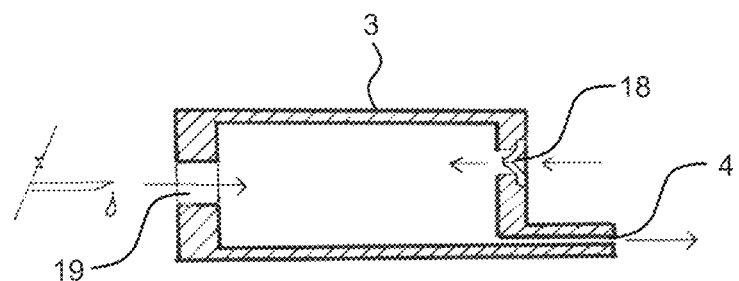
FIG. 4 is a topside view of a refillable cartridge for an aerosol-generating system according to some example embodiments.

FIG. 4 shows a refillable cartridge for an aerosol-generating system. The cartridge comprises a liquid storage portion 3 made of a rigid container. The container comprises an outlet connected via a tubing segment 4 to the inlet of the micro pump. Air is allowed to enter the rigid container via a one-way valve 18 upon pumping liquid. A septum 19 is provided for refilling the cartridge.

Figure 5:
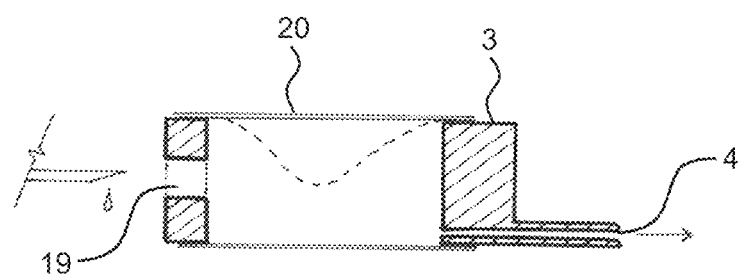
FIG. 5 is a topside view of a refillable cartridge for an aerosol-generating system according to some example embodiments.

FIG. 5 shows a refillable cartridge for an aerosol-generating system. The cartridge comprises a liquid storage portion 3 made of a rigid container with a flexible wall 20 made from a flexible tube. The container comprises an outlet connected via a tubing segment 4 to the inlet of the micro pump. Upon pumping liquid, the flexible wall 20 collapses. A septum 19 is provided at the rigid container for refilling the cartridge.

Figure 6:
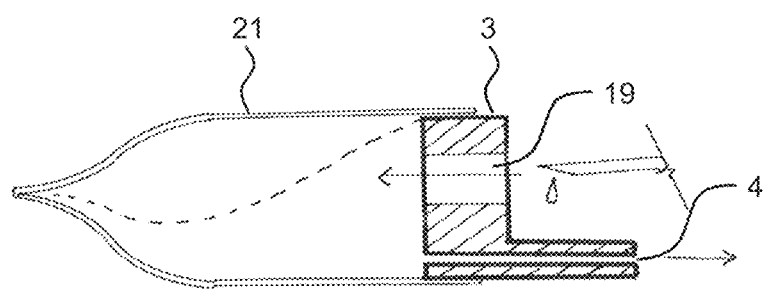
FIG. 6 is a topside view of a refillable cartridge for an aerosol-generating system according to some example embodiments.

FIG. 6 shows a refillable cartridge for an aerosol-generating system. The cartridge comprises a liquid storage portion 3 made of a rigid faceplate with two flexible walls 21 each made from a flexible tube. The container comprises an outlet connected via a tubing segment 4 to the inlet of the micro pump. Upon pumping liquid, the flexible walls 21 collapse. A septum 19 is provided at the rigid faceplate for refilling the cartridge.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

What is claimed is:

1. An aerosol-generating system, the system comprising:
   a liquid storage portion configured to hold a liquid aerosol-forming substrate, the liquid storage portion including,
      an outlet fluidly coupled to a first tubing segment,
      a one-way valve disposed in a first wall of the liquid storage portion adjacent the outlet, and
      a septum disposed in the liquid storage portion in a second wall opposite the first wall, the septum configured to enable refilling of the liquid storage portion with the liquid aerosol-forming substrate;
   a vaporizer including a heating element having a structure defining an open-ended internal passage;
   a micro pump fluidly coupled to the first tubing segment and configured to deliver liquid aerosol-forming substrate from the liquid storage portion to the internal passage of the heating element; and
   a second tubing segment configured to deliver the liquid aerosol-forming substrate from the micro pump to the internal passage of the heating element, the heating element extending from and partially overlapping an open-ended side of the second tubing segment,
   wherein the vaporizer is configured to directly heat the delivered liquid aerosol-forming substrate at the internal passage of the heating element to a temperature sufficient to volatilize at least a part of the delivered liquid aerosol-forming substrate.

2. The aerosol-generating system according to claim 1, wherein the micro pump is configured to deliver a determined amount of the liquid aerosol-forming substrate from the liquid storage portion to the internal passage of the heating element based on the micro pump performing an individual pump cycle.

3. The aerosol-generating system according to claim 1, further comprising:
   a chamber configured to receive the liquid aerosol-forming substrate delivered from the liquid storage portion by the micro pump;
   wherein the micro pump includes an outlet and the micro pump is configured to deliver the liquid aerosol-forming substrate through the outlet of the micro pump;
   wherein the heating element is located inside the chamber and proximate to the outlet of the micro pump.

4. The aerosol-generating system according to claim 1, wherein the vaporizer is arranged downstream of an open end of the second tubing segment.

5. The aerosol-generating system according to claim 1, wherein the second tubing segment includes a capillary tube.

6. The aerosol-generating system according to claim 1, wherein the vaporizer includes a heating coil extending around a portion of the second tubing segment.

7. The aerosol-generating system according to claim 1, wherein the vaporizer includes a heating coil extending from the open-ended side of the second tubing segment in a longitudinal direction.

8. The aerosol-generating system according to claim 1, wherein the liquid storage portion includes a rigid container and that the one-way valve is configured to direct air into the rigid container upon delivering the liquid aerosol-forming substrate from the liquid storage portion to the internal passage of the heating element.

9. The aerosol-generating system according to claim 1, wherein the liquid storage portion includes at least one movable wall, the at least one movable wall configured to reduce a volume of the liquid storage portion to cause liquid aerosol-forming substrate to be delivered from the liquid storage portion to the internal passage of the heating element.

10. The aerosol-generating system according to claim 1, wherein a flow rate of the delivered liquid aerosol-forming substrate through the micro pump is within 0.5 to 2 microliters per second.

11. The aerosol-generating system according to claim 1, further comprising:
a main unit and a cartridge, the cartridge configured to be removably coupled to the main unit, the main unit including a power supply, the liquid storage portion being within the cartridge, the micro pump being located in the main unit.

12. The aerosol-generating system according to claim 11, wherein the cartridge includes the liquid storage portion.

13. The aerosol-generating system according to claim 1, wherein the micro pump comprises a piezoelectric diaphragm, a first check valve at a micro pump inlet, and a second check valve at a micro pump outlet, the piezoelectric diaphragm configured to be deformed upon applying a voltage to the piezoelectric diaphragm.

14. The aerosol-generating system according to claim 1, wherein the micro pump comprises two or more micro pumps connected in series.

15. The aerosol-generating system according to claim 1, wherein the liquid storage portion comprises a rigid container with at least one flexible wall between the first wall and the second wall.

16. A method, comprising:
controlling a micro pump to deliver liquid aerosol-forming substrate from a liquid storage portion to an internal passage within a heating element of a vaporizer through a first tubing segment, the heating element extending from and partially overlapping an open ended side of the first tubing segment; and
controlling the vaporizer to directly heat the delivered liquid aerosol-forming substrate at the internal passage to a temperature sufficient to volatilize at least a part of the delivered liquid aerosol-forming substrate;
wherein the liquid storage portion includes,
an outlet fluidly coupled to a second tubing segment,
a one-way valve disposed in a first wall of the liquid storage portion adjacent the outlet, and
a septum disposed in the liquid storage portion in a second wall opposite the first wall, the septum configured to enable refilling of the liquid storage portion with the liquid aerosol-forming substrate.

17. The method according to claim 16, wherein the controlling the micro pump includes causing the micro pump to deliver a determined amount of the liquid aerosol-forming substrate from the liquid storage portion to the internal passage of the heating element based on causing the micro pump performing an individual pump cycle.

18. The method according to claim 16, wherein the controlling the micro pump includes causing the micro pump to deliver the liquid aerosol-forming substrate at a flow rate that is within 0.5 to 2 microliters per second.

19. The method according to claim 16, wherein,
the micro pump includes an outlet,
the heating element is located inside a chamber and proximate to the outlet of the micro pump, and
the controlling the micro pump includes causing the micro pump to deliver the liquid aerosol-forming substrate through the outlet of the micro pump.

* * * * *